United States Patent [19]

Hokama

[11] Patent Number: 5,525,525
[45] Date of Patent: Jun. 11, 1996

[54] IMMUNO-LATEX CHROMATOGRAPHIC PROCEDURE FOR DETECTION OF CIGUATOXIN, AND RELATED POLYETHER MARINE TOXINS

[75] Inventor: Yoshitsugi Hokama, Honolulu, Hi.

[73] Assignee: Asian Pacific Research Foundation, Honolulu, Hi.

[21] Appl. No.: 240,570

[22] Filed: May 11, 1994

[51] Int. Cl.$^6$ .................. G01N 33/12; G01N 33/543; G01N 33/546

[52] U.S. Cl. .................. 436/523; 436/534; 436/161; 436/815; 435/975

[58] Field of Search .................. 436/523, 534, 436/807, 161–162, 815; 422/57; 435/975

[56] References Cited

U.S. PATENT DOCUMENTS

| | | | |
|---|---|---|---|
| D. 342,031 | 12/1993 | Richardson | D10/81 |
| 4,816,392 | 3/1989 | Hokama | 435/7.21 |
| 5,206,141 | 4/1993 | Park | 435/7.1 |
| 5,238,652 | 8/1993 | Sun et al. | 422/61 |
| 5,266,497 | 11/1993 | Imai et al. | 436/514 |
| 5,286,498 | 2/1994 | Park et al. | 424/520 |

OTHER PUBLICATIONS

Bangs, L. B.: Latex agglutination tests. Amer. Clin. Lab News 7:(4A)20–25, 1988.

Bangs, L. B.: Latex immunoassays. J. Clin. Immunoassay 13:127–131, 1990.

Bangs, L. B.: New developments in particle–based tests and immunoassays. J. Int'l Fed. Clin. Chem. 2:(4), 188–192, 1990.

Hokama, Yoshitsugi: Simplified solid–phase immunobead assay for detection of ciguatoxin and related polyethers, J. Clin. Lab. Analy. 4:213–217, 1990.

Hokama, Y., Banner, A. H., Boyland, D. A.: A radioimmunoassay for detection of ciguatoxin. Toxicon 15:317–325, 1977.

Hokoma, Y., A rapid simplified enzyme immunoassay stick test for the detection of ciguatoxin and related polyethers from fish tissues. Toxicon 23:939–946, 1985.

Hokama, Y., Abad, M. A., Kimura, L. H.: A rapid enzyme immunoassay (EIA) for the detection of ciguatoxin in contaminated fish tissues. Toxin 21:817–824, 1983.

Hokama, Y., Honda S. A. A., Kobayashi, M. N., Nakagawa, L. K., Shirai, L. K., and Miyahara, J. T.: Monoclonal antibodies (MonoAbs) to ciguatoxin and related polyethers. In Lecture Notes on Coastal and Estuarine Studies vol. 25, Yentsch, C. M., Mague, F. C. and Horan, P. K. (eds.), Springer–Verlag, New York, pp. 155–166, 1988.

Hokama, Yoshitsugi: Recent methods for detection of seafood toxins: recent immunological methods for ciguatoxin and related polyethers, Food Additives and Contaminants, 10: (1) 71–82, 1993.

McHugh, T. M., Wang, Y. J., Chong, H.O., Blackwood, L. L., and Stites, D. P.: Development of a microsphere–based fluorescent immunoassay and its comparision to an enzyme immunoassay for the detection of antibodies to three antigen preparations from *Candida albicans*, J. Immunol. Meth., 116:213–219, 1989.

*Primary Examiner*—Toni R. Scheiner
*Assistant Examiner*—Patricia A. Duffy
*Attorney, Agent, or Firm*—Dowell & Dowell

[57] ABSTRACT

An antibody test suitable for the rapid detection of ciguatoxin and other related low molecular weight polyether marine lipid toxins in fish tissue in the field or laboratory is disclosed. The test utilizes the reaction between antibody coated, mixed latex beads and any lipids in an extract of a sample of fish tissue eluted in a solvent. The presence of toxins is determined within about thirty minutes by ascending chromatography, which separates the mixed beads. The toxin concentration is determined by reference to standard data. A kit suitable for performing the testing procedure in the field is also disclosed. The kit includes a support having a nylon membrane covering, and antibody coated, mixed beads applied on the membrane, a testing container, a supply of solvent and a biopsy tool.

22 Claims, 3 Drawing Sheets

FIG. 1

CTX  R1 = HOCH2CH—
              |
              OH
     R2 = OH     (from moray eel liver)

CTX4B R1 = CH2=CH—
      R2 = H       (from Gambierdiscus toxicus)

IMMUNO-LATEX CHROMATOGRAPHIC PROCEDURE FOR DETECTION OF CIGUATOXIN, AND RELATED POLYETHER MARINE TOXINS

BACKGROUND OF THE INVENTION

1. Field of the Invention

The invention is directed to the field of analytical and immunological testing, and more particularly, to a method for testing organic extracts of organisms, vertebrate and invertebrate tissues, and microorganisms, using synthetic membranes in conjunction with antibody binding assays and antigen-antibody reactions, especially with lipid epitopes (haptens or determinants). The reactions utilize a chromatographic phase in which extracted lipid toxins in a solvent migrate toward mixed antibody coated latex beads provided on a solid phase nylon membrane. The reactions may also involve complex formation by antibody-antigen reactions in the liquid phase. Separation techniques for removing complexes from unbound antigens or antibodies are used.

2. History of the Related Art

The use of latex coated with an antibody for detecting antigens has been known in the clinical art, and especially in the area of visible agglutinative reactions. The procedure is sufficiently specific and sensitive for accurate qualitative and quantitative determinations.

The art has recognized radioimmunoassay, agglutination and enzyme immunoassay, in both direct and competitive binding assays. In the area of latex immunoassay, colored latex beads having specific antibodies bound to their surface, either chemically or by absorption, are used as a tag for antibodies. The so-called dipstick enzyme or chemical immunoassay test is used for rapidly generating qualitative and semi-quantitative information regarding the presence of analytes.

There has long been a need for a rapid and simple to perform procedure for distinguishing edible from potentially toxic fish; in particular, a procedure for detecting ciguatoxins and related low molecular weight polyether marine toxins in fish indigenous to regions where the ecological microflora which cause ciguatera are found. The major source of ciguatoxin is *Gambierdiscus toxicus* (*G. toxicus*) discovered in 1977 at Gambier Island, French Polynesia. Ciguatoxin has been determined to be the major cause of ciguatera fish poisoning in the tropical and subtropical regions of the world. Ciguatoxin is a marine polyether which is synthesized by *G. toxicus* and then proceeds up the food chain through herbivorous fish and carnivorous fish (e.g., amberjacks, jacks, snappers, groupers, moray eels and barracuda). Ciguatoxin-4B (CTX-4B) from *G. toxicus* is converted to ciguatoxin-1 (CTX-1) in the moray eel liver.

Because more than 24 ciguatoxins (congeners) have been reported, it is unknown whether all species of carnivorous fish associated with ciguatera convert CTX-4B to CTX-1. Thus, a test procedure for analyzing suspect fish flesh should be capable of assessing all congeners and related polyethers, such as maitotoxin, okadaic acid, brevetoxin and palytoxin, although the toxicity of the congeners may vary. These toxins, and especially ciguatoxin and its related polyether congeners, are able to maintain resinous and fatty substances in suspension in water and are highly irritating in their pure form to the skin or mucous membrane.

If ciguatoxin is present in fish tissue or mucous membrane and consumed by humans, it can cause severe ciguatera food poisoning. Such poisoning may cause gastrointestinal, neurological and cardiovascular disorders, and a number of general symptoms. Possible gastrointestinal disorders are vomiting, nausea, stomach pains and diarrhea. Neurological symptoms may include paresthesia and dysesthesia. Cardiovascular effects include bradycardia and tachycardia. General symptoms include taste and vision alteration, itching and weakness, and the most severe general symptoms are muscle aches and joint pains which may persist for months.

SUMMARY OF THE INVENTION

The present invention has been made in view of the above-described inadequacies of the related art and has as an object to provide a method for detecting ciguatoxin, its congeners and related polyether toxins in fish tissue prior to human consumption.

It is also an object of the invention to provide a method that is simple to perform and provides test results in a short period of time so that the method may be used on location by individuals to sort edible from potentially toxic fish.

It is a further object of the invention to provide a field test kit for performing the method in accordance with the invention.

Additional objects and advantages of the present invention will become apparent from the detailed description which follows, considered in conjunction with the accompanying drawing figures, or by practice of the invention.

To achieve the objects of the invention, as embodied and broadly described herein, the method for detecting ciguatoxin, its congeners and related polyether marine toxins in fish tissue in accordance with a preferred embodiment of the invention comprises providing a support having a front face and a bottom face, and first latex beads of a first diameter and second latex beads of a second relatively larger diameter disposed on the front face. The latex beads are coated with an anti-ciguatoxin which is capable of recognizing ciguatoxin and related polyether marine toxins.

The method further comprises providing a volume of a solvent and a sample of fish tissue. The fish tissue is immersed in the solvent for a sufficient amount of time to produce an extract.

The extract is tested by subsequently immersing the support in the extract such that the first and second latex beads are positioned above and proximate to the meniscus. The support is immersed in the extract for a sufficient amount of time to enable the first latex beads to move a distance on the support relative to the second latex beads so as to indicate the presence of any ciguatoxin and related polyether marine toxins in the extract.

The results of the extract testing are analyzed by measuring the distance moved by the first latex beads relative to the second latex beads, and comparing this distance to standard data representing known ciguatoxin concentration versus known distance to determine the ciguatoxin concentration in the fish tissue.

The invention also comprises a kit suitable for performing the method of the invention in the field and laboratory.

BRIEF DESCRIPTION OF THE DRAWINGS

In the accompanying drawings:

FIG. 1 represents the chemical structure of ciguatoxin;

DETAILED DESCRIPTION OF THE PREFERRED EMBODIMENT

The invention is a method for testing suspect fish tissue to detect the presence of ciguatoxin, its congeners and related low molecular weight polyether marine toxins such as maitotoxin, okadaic acid, brevetoxin and palytoxin, and a kit for performing the method. The method is simple to perform, yields rapid results and requires a minimum number of reagents and other testing materials. The method is suitable for field and laboratory use.

In the method in accordance with the invention, latex beads of two different colors and diameters are coated with anti-ciguatoxin (antibody) in a buffered saline suspension. The antibody is directed to recognizing ciguatoxin and related polyether marine toxins. The antibody may be polyclonal or monoclonal and may be produced by a conventional technique. The latex-antibody mixture is spotted on a nylon membrane near the bottom end of a support.

A fish extract is prepared by removing a piece of fish tissue from a suspect fish, using a biopsy tool to form a fish tissue sample and placing the sample in a container holding a volume of solvent.

The extract is tested for the presence of ciguatoxins, its congeners and related polyethers, by partially immersing the support in the solvent extract. If any ciguatoxin and related polyethers are present in the extract, the solvent solution migrates on the support by ascending chromatography and the CTX in the extract reacts with the anti-ciguatoxin coating on the latex beads to form CTX—Ab—CTX complexes and increase the polarity of the antibody coating. This physical change causes the smaller sized beads to separate and migrate within a short period of time while the larger beads essentially remain stationary. If no lipid ciguatoxin is present to bind with the antibody coating and no complexes form, the polarity of the coating is essentially unchanged. No migration occurs in such instances because the solvent is unable to separate the polar beads with the coated anti-ciguatoxin (protein).

The method in accordance with the invention uses known test conditions to ensure consistent results. Semi-quantitative test information is obtained by measuring the distance between the mobile front of the smaller beads and the stationary large bead front. The unknown quantity of ciguatoxin in the fish tissue is determined by referring to standard data obtained from known concentrations of ciguatoxin and corresponding distance migrated by latex beads in an ascending chromatogram.

The testing procedure comprises initially removing a piece of fish tissue from a suspect fish using a conventional cutting tool such as a knife. The fish tissue is preferably removed in the form of a cube having approximately one-inch sides.

Figure 2A:
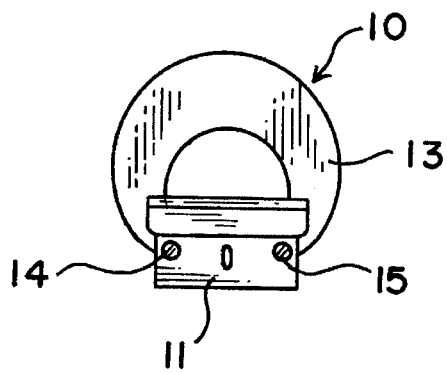
FIG. 2A is a front elevational view of a biopsy tool for use in the method in accordance with the invention.
Figure 2B:
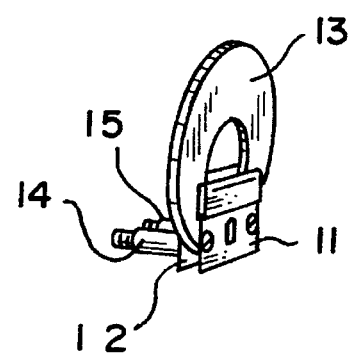
FIG. 2B is a side perspective view of the biopsy tool of FIG. 2A.

The fish tissue is next cut into one or more smaller samples of a suitable size for subsequent testing. FIGS. 2A and 2B illustrate a biopsy tool 10 preferably used for this purpose. The biopsy tool includes a pair of parallel cutting blades 11, 12 secured to a generally C-shaped handle 13 by screws 14, 15. The biopsy tool is used to prepare samples preferably in the form of cubes having approximately 2 mm sides. Such samples have a weight of approximately 5 mg based on the density of the fish tissue.

FIGS. 6–9 illustrate the manner of performing a field latex-antibody chromatographic test for detecting ciguatoxin, its congeners and related polyether toxins in a prepared fish tissue sample.

Figure 6:
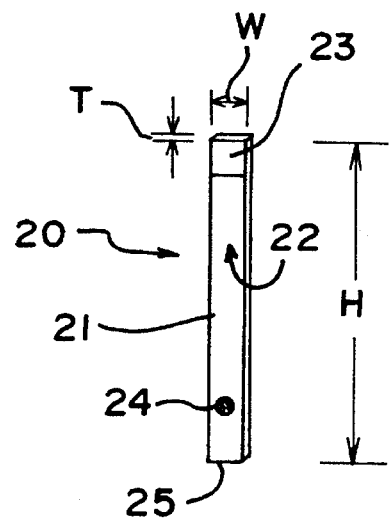
FIG. 6 illustrates a support for use in the method in accordance with the invention.

FIG. 6 illustrates a support 20 preferably composed of a solid plastic material on which a nylon membrane 21 having a pore size of about 0.45μ is adhered. The membrane may be adhered by a suitable adhesive such as double-sided tape or the like. The support preferably has a height H of about 80 mm, a width W of about 5 mm and a thickness T of about 1 mm. The membrane preferably covers a substantial portion of the front face 22 of the support and an area 23 approximately 10 mm in height is uncovered at the top portion of the support.

The anti-ciguatoxin (protein) is preferably added to the latex bead mixture at a concentration of about 0.5 mg/ml of a 2% suspension of the beads. Approximately 100 μl of the latex bead and antibody mixture is applied on the membrane in the form of a spot 24 located about 15 mm above the bottom face 25 of the support. The latex beads preferably comprise a plurality of red colored beads of about 0.177μ diameter and a plurality of blue colored beads of about 0.318μ diameter.

Figure 7:
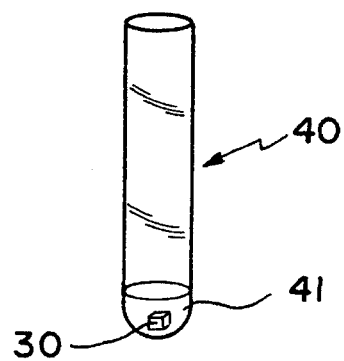
FIG. 7 illustrates the elution of a sample of fish tissue in the solvent to form an extract.

As depicted in FIG. 7, a fish tissue sample 30 is immersed in about 1 ml of a solvent 41 contained in a test tube 40 or a like container having an open end. The solvent is preferably absolute methanol. For single test usage, the test tube is provided with a 1 ml supply of methanol.

Figure 3:
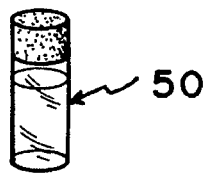
FIG. 3 illustrates a vial containing a volume of a solvent for use in the method in accordance with the invention.
Figure 4:
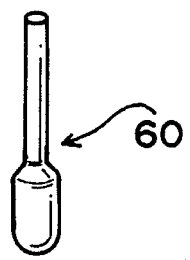
FIG. 4 illustrates a dropper for dispensing the solvent of FIG. 3.

Alternatively, for the testing of a plurality of fish tissue samples, a plurality of supports and a separate closed vial 50 containing approximately 1 ml of methanol for each support are provided. See FIG. 3. In such instances, a dropper 60 such as illustrated in FIG. 4 is also provided for dispensing 1 ml amounts of the solvent.

For each test, the fish tissue is immersed in the methanol for a sufficient amount of time to form a fish extract. This period is preferably about fifteen minutes.

Figure 8:
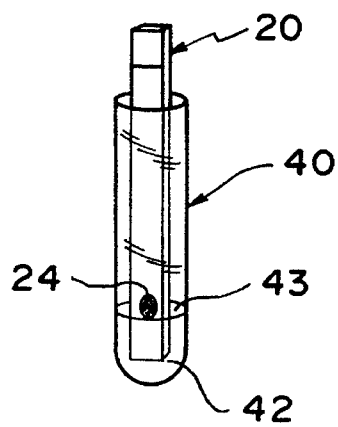
FIG. 8 illustrates the manner of immersing the support of FIG. 6 in the extract to test the extract for the presence of ciguatoxin and related polyether marine toxins.

Referring to FIG. 8, after the fish tissue has been immersed in the test tube for a sufficient amount of time, the extract is tested for the presence of ciguatoxins and related polyether marine toxins by partially immersing the support 20 in the methanol extract 42 such that the latex beads 24 are positioned above and proximate to the meniscus level 43 of the extract. The support is preferably maintained in this position for a sufficient amount of time for the smaller sized latex beads to ascend on the support relative to the larger latex beads to indicate the presence of any ciguatoxin and related polyether marine toxins in the extract. The immersion time for the support is preferably between about 15 to 30 minutes and, more preferably, about 15 minutes.

Figure 5:
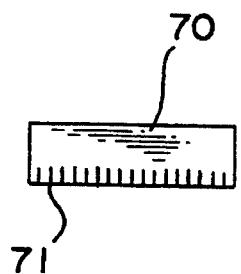
FIG. 5 illustrates a measuring device for use in the method in accordance with the invention.
Figure 9:
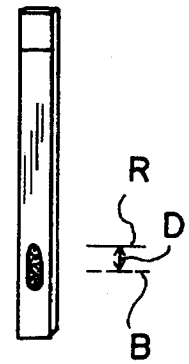
FIG. 9 illustrates the separation of the latex beads on the support of FIG. 6 following its immersion in the extract.

After the support has been immersed for a sufficient amount of time, it is removed from the extract and test tube. Referring to FIG. 9, the distance D between the uppermost position of the stationary front of the blue beads B and the uppermost position of mobile front of the red beads R is measured. A suitable measuring tool 70 for this purpose is illustrated in FIG. 5 preferably having spaced increments 71 of 1 mm. The measured distance is compared to a standard curve or other tabulated data prepared from data for known ciguatoxin concentration and corresponding latex bead separation distance determined for a range of ciguatoxin concentrations by the ascending chromatographic technique in accordance with the invention.

If the measured separation of the latex bead fronts is greater than about 2.0 mm, the known ciguatoxin concentration of the fish which corresponds to this distance is considered excessive for human consumption and the fish is inedible. If the separation distance is less than about 1.75 mm, the ciguatoxin concentration in the fish is considered to be safe for human consumption. Intermediate values between about 1.75 mm and 2.0 mm represent ciguatoxin concentrations in the fish of questionable safety for human consumption.

The foregoing description of the preferred embodiment of the invention has been presented to illustrate the principles of the invention and not to limit the invention to the particular embodiment illustrated. It is intended that the scope of the invention be defined by all of the embodiments encompassed within the following claims and their equivalents.

What is claimed is:

1. A method for detecting ciguatoxin and structurally related polyether marine toxins in fish tissue, comprising the steps of:

providing a support having a surface, a porous membrane disposed on said surface, first latex beads of a first diameter and a first color and second latex beads of a second diameter and a second color being disposed at a common position on said membrane, said second diameter being larger than said first diameter, and said first and second latex beads having a coating of anti-ciguatoxin antibody for recognizing ciguatoxin and related polyether marine toxins;

immersing fish tissue in a solvent for a sufficient amount of time to produce an extract;

immersing said support in said extract to position said first and second latex beads above and proximate to the meniscus of said extract, said support being maintained in said extract for a sufficient amount of time for said first latex beads to move a separation distance on said front surface relative to said second latex beads to indicate the presence of ciguatoxin and related polyether marine toxins in said extract; and determining the concentration of ciguatoxin and related polyether marine toxins in said fish tissue based on said separation distance.

2. The method of claim 1, wherein said fish tissue is immersed in said solvent for about 15 minutes.

3. The method of claim 2, wherein said support is immersed in said extract for between about 15 to 30 minutes.

4. The method of claim 3, wherein said support is immersed for about 15 minutes.

5. The method of claim 1, wherein said fish tissue is of a weight of about 5 mg, said solvent is methanol and said volume is about 1 ml.

6. The method of claim 1, wherein said membrane is composed of nylon and has a pore size of about $0.40\mu$.

7. The method of claim 6, wherein said first diameter is $0.117\mu$, said second diameter is $0.318\mu$, said support having a bottom surface and said first and second latex beads being positioned on said membrane about 15 mm above said bottom surface.

8. The method of claim 7, wherein said anti-ciguatoxin antibody is applied to said first and second latex beads at a concentration of about 0.5 mg/ml of 2% buffered saline suspension of the beads to form said coating, and about 100 $\mu$l of the latex bead and anti-ciguatoxin antibody mixture is applied on said membrane.

9. A method for detecting ciguatoxin and structurally related marine toxins in fish tissue, comprising the steps of:

providing a support having a front surface and a bottom surface, a porous nylon membrane being disposed on said front surface, first latex beads of a first color and a first diameter and second latex beads of a second color and a second diameter being located at a common position on said membrane above said bottom surface, said second diameter being greater than said first diameter, said first and second latex beads having a coating of anti-ciguatoxin antibody for recognizing ciguatoxin and related polyether marine toxins;

immersing fish tissue in a solvent to form an extract;

immersing said support in said extract such that said first and second latex beads are positioned above and proximate to the meniscus of said extract, said support being immersed for an effective amount of time to enable said first latex beads to ascend on said front surface relative to said second latex beads indicating the presence of ciguatoxin and related polyether marine toxins in said extract; and determining the concentration of ciguatoxin and related polyether marine toxins in said fish tissue based on the distance between said first and second latex beads.

10. The method of claim 9, wherein said anti-ciguatoxin is applied to said first and second latex beads at a concentration of about 0.5 mg/ml of 2% buffered saline suspension of the beads to form said coating, and about 100 $\mu$l of the latex bead and anti-ciguatoxin mixture is applied on said membrane.

11. A kit suitable for detecting ciguatoxin and structurally related polyether marine toxins in fish tissue, comprising:

a support having a surface, a porous membrane provided on said surface, first latex beads of a first color and first diameter and second latex beads of a second color and second diameter being disposed at a common position on said membrane, said first and second latex beads having an anti-ciguatoxin antibody coating directed to recognizing ciguatoxin and related polyether marine toxins; and a solvent effective to produce an extract from fish tissue.

12. The kit of claim 11, wherein said porous membrane is composed of nylon and has a pore size of about $0.40\mu$, said first diameter is about $0.177\mu$, and said second diameter is about $0.318\mu$.

13. The kit of claim 12, wherein said anti-ciguatoxin antibody being applied to said first and second latex beads at a concentration of about 0.5 mg/ml of 2% buffered saline suspension of the beads to form said coating, and about 100 $\mu$l of the latex bead and anti-ciguatoxin antibody mixture is applied on said membrane.

14. The kit of claim 12, wherein said solvent is methanol.

15. The kit of claim 11, further comprising a source of standard data representing known ciguatoxin concentration and corresponding distance of separation of latex beads.

16. The kit of claim 11, comprising a plurality of supports.

17. The kit of claim 14, further comprising a dropper and a container of methanol.

18. The kit of claim 17, further comprising means for preparing fish tissue samples.

19. The kit of claim 15, further comprising means for measuring separation distance of said first and second latex beads on said porous membrane.

20. The kit of claim 11, wherein said membrane covers a portion of said surface and the remaining portion of said surface is uncovered.

21. A method for detecting ciguatoxin in fish tissue, comprising the steps of:

providing a support having a surface, a porous membrane disposed on said surface, first latex beads of a first diameter and a first color and second latex beads of a second diameter and a second color being disposed at a common position on said membrane, and said first and second latex beads having a coating of anti-ciguatoxin antibody for recognizing ciguatoxin;

immersing fish tissue in a solvent to produce an extract;

placing said support in said extract to position said first and second latex beads above and proximate to the meniscus of said extract, said support being maintained in said abstract for an effective amount of time for said first latex beads to ascend on said front surface relative to said second latex beads to indicate the presence of ciguatoxin in said extract; and determining the concentration of ciguatoxin in said fish tissue based on the distance between said first and second latex beads.

22. A kit for detecting ciguatoxin in fish tissue, comprising:

a support having a surface, a porous membrane provided on said surface, first latex beads of a first color and a first diameter and second latex beads of a second color and a second diameter being disposed at a common position on said membrane, said first and second latex beads having an anti-ciguatoxin antibody coating for recognizing ciguatoxin; and means for producing an extract from fish tissue.

\* \* \* \* \*